United States Patent [19]

Kimura et al.

[11] 4,224,113
[45] Sep. 23, 1980

[54] METHOD OF DETECTING AIR/FUEL RATIO IN COMBUSTOR BY DETECTING OXYGEN IN COMBUSTION GAS

[75] Inventors: Shinji Kimura, Yokohama; Hiroshi Takao, Kamakura; Shigeo Ishitani, Yokosuka; Kenji Ikezawa; Hiroyuki Aoki, both of Yokohama, all of Japan

[73] Assignee: Nissan Motor Company, Limited, Yokohama, Japan

[21] Appl. No.: 28,747

[22] Filed: Apr. 10, 1979

[30] Foreign Application Priority Data

Nov. 2, 1978 [JP] Japan ................................ 53-135296

[51] Int. Cl.$^2$ ............................................. G01N 27/58
[52] U.S. Cl. .................................. 204/1 T; 204/195 S
[58] Field of Search ............................ 204/195 S, 1 S; 123/119 E, 119 EC; 60/276; 324/29; 422/98

[56] References Cited

U.S. PATENT DOCUMENTS 4,107,019  8/1978  Takao et al. ...................... 204/195 S

OTHER PUBLICATIONS

David S. Howarth et al., SAE 780212, (1978).

G. L. Beaudoin et al., SAE 760312, (1976).

*Primary Examiner*—G. L. Kaplan
*Attorney, Agent, or Firm*—Schwartz, Jeffery, Schwaab, Mack, Blumenthal & Koch

[57] ABSTRACT

A method of detecting numerical values for air/fuel ratio of either a lean air-fuel mixture or a rich mixture supplied to, for example, a combustion engine by means of an oxygen sensor disposed in the exhaust gas. The sensor comprises a porous measurement electrode layer on one side of a porous solid electrolyte layer, e.g., of zirconia and a porous reference electrode layer on the other side with a shield layer thereon, so that the reference electrode layer communicates with the exhaust gas through pores in the sensor. Measurement is accomplished by keeping a DC current flowing between the two electrode layers to establish a reference oxygen partial pressure on the reference electrode side. The intensity of the current is made below a critical value above which an EMF generated by the sensor becomes substantially constant unless the air/fuel ratio changes across the stoichiometric ratio, and the direction of the current flow is chosen depending on whether the air-fuel mixture is a lean one or a rich one.

8 Claims, 24 Drawing Figures

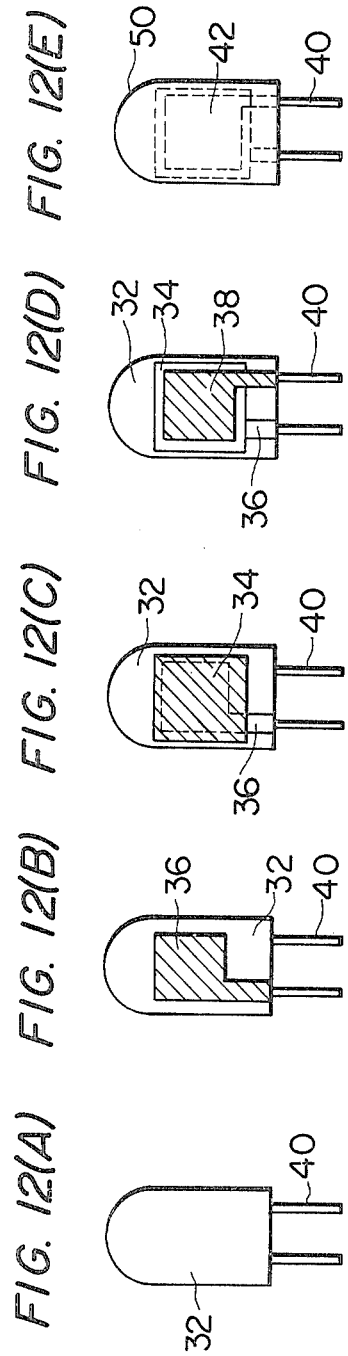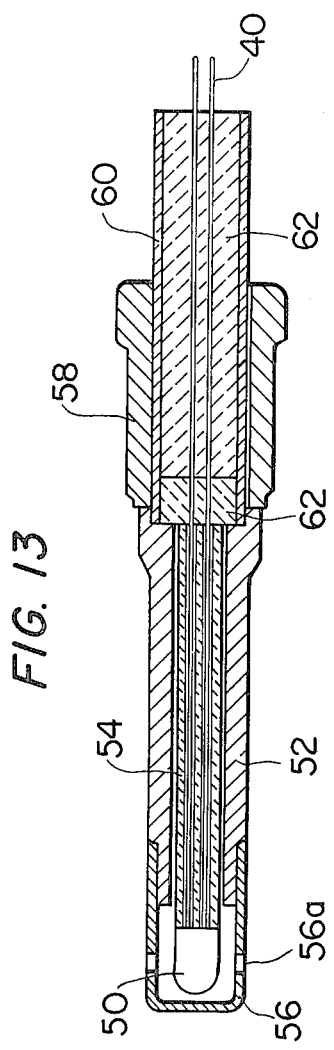

METHOD OF DETECTING AIR/FUEL RATIO IN COMBUSTOR BY DETECTING OXYGEN IN COMBUSTION GAS

BACKGROUND OF THE INVENTION

This invention relates to a method of detecting the air/fuel ratio of an air-fuel mixture subjected to combustion in a combustor, such as a combustion chamber of an internal combustion engine, by using an oxygen sensor of a specific type disposed in the combustion gas exhausted from the combustor.

In the field of internal combustion engines, particularly in automotive engines, it has been popularized to detect changes in the air/fuel ratio of an air-fuel mixture actually supplied to the engine as the basis for feedback control of the air/fuel ratio by detecting changes in the concentration of oxygen in the exhaust gas of the engine, since it is more practical to provide an oxygen sensor to the exhaust system of the engine than to the intake system. An oxygen sensor prevailing for this purpose is of the concentration cell type having a layer of an oxygen ion conductive solid electrolyte, a measurement electrode layer porously formed on one side of the solid electrolyte layer and a reference electrode layer formed on the other side. This oxygen sensor is used with the maintenance of a reference oxygen partial pressure at the interface between the reference electrode layer and the solid electrolyte layer, so that the sensor generates an electromotive force, the magnitude of which varies according to a difference between an oxygen partial pressure in a sample gas to which is exposed the measurement electrode layer and the reference oxygen partial pressure. When used in an engine exhaust gas, this oxygen sensor exhibits a great and sharp change in its output on the occurrence of a change in the air/fuel ratio across a stoichiometric air/fuel ratio. Accordingly this oxygen sensor is quite suitable in the case of an engine being operated with a stoichiometric or a nearly stoichiometric air-fuel mixture.

In automotive gasoline engines, the development of so-called lean-burn-engines has been in progress with the view of improving the combustion efficiency and as a consequence further advancing the exhaust emission control by the employment of a considerably lean air-fuel mixture, i.e. a mixture having an air/fuel ratio considerably above the stoichiometric air/fuel ratio 14.7 (by weight).

In lean-burn-engines, however, the control of the air/fuel ratio encounters a problem that it is impossible to accurately detect or estimate an actual air/fuel ratio of a lean mixture by the installation of an oxygen sensor of the above described type in the exhaust system since there occurs little change in the magnitude of the electromotive force of the sensor when the air/fuel ratio changes only on one side of the stoichiometric ratio. Therefore, conventional lean-burn-engines are compelled to employ open-loop air/fuel ratio control systems which require the addition of various elements to the engine intake system. However, these control systems are disadvantageous not only in their complicatedness and expensiveness but also in their unsatisfactory accuracy and responsiveness.

A method of detecting a lean air/fuel ratio is proposed in SAE Paper (Society of Automotive Engineers, U.S.A.) No. 78.0212 (1978). In this method, use is made of an oxygen sensor having a tubular layer of zirconia (a typical example of oxygen ion conductive solid electrolytes) which is coated with reference and measurement electrode layers respectively on the inside and on the outside with compensation for temperature and using air as the source of the reference oxygen partial pressure.

However, the magnitude of changes in an electromotive force generated by the oxygen sensor disposed in the exhaust gas and used in this manner is very small insofar as the air/fuel ratio varies within a lean range, so that it is not easy to accomplish feedback control of the air/fuel ratio based on the output of the oxygen sensor. For example, an oxygen partial pressure P in the exhaust gas is about $1 \times 10^{-2}$ atm when the air/fuel ratio is about 15 and becomes about $4 \times 10^{-2}$ atm when the air/fuel ratio varies to about 18, while the reference oxygen partial pressure (of air) $P_o$ is about 0.21 atm. According to the Nernst Equation, the magnitude of a change $\Delta E$ in the electromotive force resulting from the change of the oxygen partial pressure P from $P_1 = 1 \times 10^{-2}$ to $P_2 = 4 \times 10^{-2}$ at a constant temperature T (°K.) is expressed as follows:

$$\Delta E = \frac{RT}{4F} \left( \ln \frac{P_o}{P_1} - \ln \frac{P_o}{P_2} \right) = \frac{RT}{4F} \ln \frac{P_2}{P_1} = $$
$$0.0496 T \times \log_{10} \frac{P_2}{P_1} \text{ (mV)}$$

where R is the gas constant and F is the Faraday constant. When the exhaust gas temperature T is 900° K., $$\Delta E = 0.0496 \times 900 \times \log_{10} \frac{4 \times 10^{-2}}{1 \times 10^{-2}} = 27 \text{ mV}$$

This value for $\Delta E$ is too small to utilize as a feedback signal in a practical air/fuel ratio control system since various factors such as dispersion in electromotive force generating ability of industrially produced oxygen sensors, influence of the exhaust gas temperature on the electromotive force and errors in the measurement by the influence of noises must be taken into consideration.

According to SAE Paper No. 76.0312 (1976), it is possible to detect changes in air/fuel ratio of a lean mixture by utilizing a certain oxide semiconductor such as CoO, which exhibits a change in its resistivity in response to a change in an oxygen partial pressure in an environmental gas atmosphere, as the sensitive element of an oxygen sensor which is disposed in the exhaust gas. It is necessary, however, to maintain this sensitive element at a very high temperature such as about 900° C. because at lower temperatures CoO tends to transform into more stable $Co_3O_4$ of which the resistivity is not significantly influenced by an oxygen partial pressure in an eivironmental gas atmosphere.

Accordingly an oxygen sensor of this type needs to be provided with a heater. In practical applications, the provision of a heater which is continuously operated at a temperature as high as 900° C. offers various problems such as deterioration of not only the heater material but also the CoO sensing element itself and complicatedness of an indispensable temperature compensation circuit. Because of these problems, this sensor is unsuitable for use in popular apparatus such as automobiles.

U.S. Pat. No. 3,941,673 shows a zirconia tube oxygen sensor which utilizes a noncatalytic material such as gold or silver as the material of its measurement electrode layer to be exposed to an engine exhaust gas and is of use for detection of air/fuel ratios of a rich mixture. From a practical viewpoint, however, this oxygen sensor is unsatisfactory in that the measurement electrode layer is insufficient in its endurance in a high temperature and high velocity fluid flow such as an exhaust gas in an automotive engine exhaust line because of a relatively low melting point and softness of the electrode material and in that the relationship between oxygen partial pressure in a sample gas and electromotive force of the sensor tends to fluctuate because of adsorption of the sample gas in the noncatalytic electrode layer. Besides, as a shortcoming common to conventional oxygen sensors comprising a zirconia tube large enough to serve as a structural member, a temperature compensation circuit for this oxygen sensor (to compensate for changes in the electromotive force with changes in temperature) becomes considerably more costly because of a large heat capacity of the zirconia tube.

SUMMARY OF THE INVENTION

Concerning an apparatus having a combustor or combustion chamber in which is burned an air-fuel mixture and an exhaust conduit through which is passed a combustion gas, as typified by an internal combustion engine, it is an object of the present invention to provide an improved and practicable method of detecting an actual air/fuel ratio of the mixture burned in the combustion chamber by the use of an oxygen sensor disposed in the exhaust gas conduit, which method is effective either when the air-fuel mixture is a lean mixture or when the air-fuel mixture is a rich mixture.

It is another object of the invention to provide a method of detecting the concentration of oxygen in a combustion gas produced by combustion of an air-fuel mixture having an air/fuel ratio either above or below the stoichiometric air/fuel ratio.

According to a method of the present invention, an actual air/fuel ratio of an air-fuel mixture subjected to combustion in an apparatus having a combustion chamber and an exhaust conduit through which passes a combustion gas produced by burning of the air-fuel mixture in the combustion chamber is detected by the following steps. In this method use is made of an oxygen sensing probe which comprises a gas permeably porous layer of an oxygen ion conductive solid electrolyte, a gas permeably porous and electronically conductive measurement electrode layer formed on and in intimate contact with one side of the solid electrolyte layer, a gas permeably porous and electronically porous reference electrode layer formed on and in intimate contact with the other side of the solid electrolyte layer and a shield layer which is made of an electrochemically inactive material and covers the reference electrode layer such that the reference electrode layer communicates with an environmental gas atmosphere only through pores in the measurement electrode layer and the solid electrolyte layer. This probe is disposed in the exhaust conduit so as to be exposed to the combustion gas, and a DC voltage is continuously applied across the measurement and reference electrode layers so as to keep a DC current of a predetermined intensity flowing through the solid electrolyte layer between the measurement and reference electrode layers thereby to maintain an oxygen partial pressure at the interface between the reference electrode layer and the solid electrolyte layer. In this state, an electromotive force generated across the measurement and reference electrode layers is measured thereby to detect the air/fuel ratio based on a predetermined relationship between the air/fuel ratio and the magnitude of the electromotive force. In this method, the predetermined intensity of the current is made smaller than a critical current intensity above which the aforementioned electromotive force becomes substantially constant insofar as the air/fuel ratio changes only on one side of the stoichiometric air/fuel ratio of the air-fuel mixture.

Where the air/fuel ratio of the air-fuel mixture is higher than the stoichiometric air/fuel ratio, the reference electrode layer of the oxygen sensing probe is connected to the negative output terminal of a DC power source for application of the DC voltage to the probe. Where the air/fuel ratio is lower than the stoichiometric ratio, the reference electrode layer is connected to the positive output terminal of the DC power source.

The oxygen sensing probe in the method according to the invention is disclosed in U.S. patent application Ser. No. 12,763 filed Feb. 16, 1979 by Kimura et al (assigned to the assignee of the present application). This probe is characterized primarily by the communication of the reference electrode layer with an external gas atmosphere subject to measurement through pores in the measurement electrode layer and the solid electrolyte layer and that a reference oxygen partial pressure is maintained on the reference electrode side of the solid electrolyte layer (without using any extra substance as a reference oxygen source) by a current made to flow through the electrolyte layer to cause electrolytic oxidation of oxygen ions and electrolytic reduction of oxygen molecules respectively in the porous measurement and reference electrode layers, or the reverse. Concerning internal combustion engines, the above referred prior application teaches that it is possible to detect a change in an air/fuel ratio realized in the engine across the stoichiometric air/fuel ratio with quick response by operating this oxygen sensing probe in the exhaust gas.

We have taken this oxygen sensing probe to be an agglomeration of a numerous number of microscopic oxygen concentration cells each having one gas passage connecting the measurement electrode layer to the reference electrode layer through the solid electrolyte layer and discovered that, by operating this probe in an engine exhaust gas with the maintenance of a controlled DC current flowing between the measurement and reference electrode layers, it is possible to accurately detect changes in the air/fuel ratio of either a lean air-fuel mixture or a rich air-fuel mixture supplied to the engine.

It will be apparent that if desired the concentration of oxygen in a combustion gas can be numerically detected by the above stated air/fuel ratio detection method according to the invention. In such a case it is necessary to preexamine the relationship between the oxygen concentration and the magnitude of the electromotive force instead of the relationship between the air/fuel ratio and the magnitude of the electromotive force.

The invention is applicable not only to combustion engines such as automotive internal combustion engines but also to various types of combustion apparatus as exemplified by industrial burners and heating apparatus.

The mechanism of the function of this probe in the present invention will be described hereinafter more in detail along with description of preferred embodiments of the invention.

BRIEF DESCRIPTION OF THE DRAWINGS

FIGS. 12(A) to 12(E) illustrate a process of fabricating an oxygen sensing element having the fundamental construction of FIG. 1;

FIG. 13 is a longitudinal sectional view of a practical oxygen sensor comprising the oxygen sensing element fabricated through the steps of FIGS. 12(A)-12(E);

DESCRIPTION OF THE PREFERRED EMBODIMENTS

Figure 1:
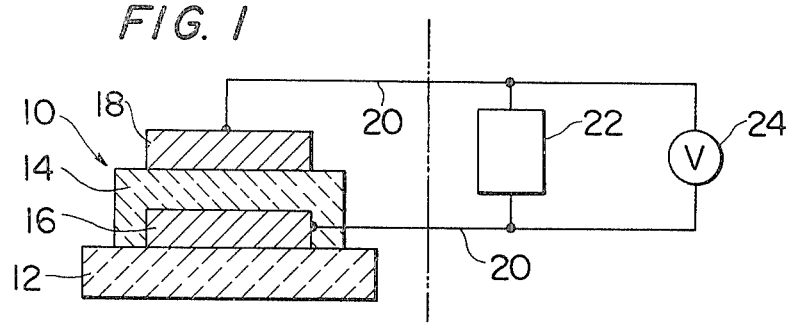
FIG. 1 shows, in a schematic and sectional view, a fundamental construction of an oxygen sensor for use in a method of the invention.

FIG. 1 shows a fundamental construction of oxygen sensors for use in an air/fuel ratio detection method according to the invention. In this illustration, an oxygen sensing element 10 has a base plate or substrate 12, which in this case serves as a structurally basic member of the sensing element 10, a microscopically porous layer 14 of an oxygen ion conductive solid electrolyte supported by the substrate 12, a measurement electrode layer 18 formed on the outside of the solid electrolyte layer 14 and a reference electrode layer 16 which is interposed between the substrate 12 and the solid electrolyte layer 14 so as to be entirely shielded from the environmental atmosphere.

The substrate 12 has a dense structure substantially impermeable to gases and usually is made of an electrically insulating ceramic material such as alumina, mullite, spinel or forsterite but, if desired, may be of an electrically conducting material such as steel, platinum, corrosion-resistant alloy or cermet. The material of the solid electrolyte layer 14 is selected from oxygen ion conductive solid electrolyte systems used for conventional oxygen sensors of the concentration cell type. Examples are $ZrO_2$ stabilized with, for example, CaO, MgO, SrO, $WO_3$, $Ta_2O_5$ or $Y_2O_3$; $Bi_2O_3$ added with $Nb_2O_5$, SrO, $WO_3$ or $Ta_2O_5$; $ThO_2$—$Y_2O_3$ system and CaO—$Y_2O_3$ system. This layer 14 may be formed by sputtering, vacuum evaporation or firing of a solid electrolyte paste applied onto the substrate 12 after the formation of the reference electrode layer 16. Also it is possible that the solid electrolyte layer 14 takes the form of a sufficiently thick plate obtained, for example, by machining a sintered body of a selected material such that this layer 14 serves as a structurally basic member of the sensing element 10 while the substrate 12 is modified to a far thinner layer merely serving as a shield coating on the reference electrode layer 16. The two electrode layers 16 and 18 are each made of an electronically conductive material selected from electrode materials for conventional oxygen sensors utilizing a solid electrolyte. Examples are Au, Ag, SiC, $ThO_2$, CoO and $LaCrO_3$ which do not exhibit any catalytic activity on oxidation reactions and catalytic metals such as Ru, Pd, Rh, Os, Ir and Pt, including alloys of these platinum group metals and alloys of a platinum group metal with a base metal. Both of the two electrode layers 16 and 18 are formed so as to be permeable to gases by sputtering, vacuum evaporation, an electro-chemical process (such as plating) or firing of a metal powder paste printed onto the substrate 12 or the solid electrolyte layer 14. Both the substrate 12 and the solid electrolyte layer 14 are in close contact with the reference electrode layer 16.

If desired, either only the outside of the measurement electrode layer 16 or the entire outer surfaces of this element 10 may be coated with a porous protective layer of a heat-resistant and electrically insulating material such as alumina, spinel or calcium zirconate ($CaZrO_3$) by sputtering, plasma spraying or firing of a paste.

In a method according to the invention, the reference and measurement electrode layers 16 and 18 of this oxygen sensing element 10 are connected to a potentiometer 24 or an equivalent means by leads 20 to measure an electromotive force the element 10 generates when disposed in a gas containing oxygen. In addition, a DC power source 22 is connected to the two electrode layers 16 and 18 in parallel with the potentiometer 24 to make a DC current flow through the solid electrolyte layer 14 between the two electrode layers 16 and 18 during operation of the oxygen sensing element 10. To avoid influences of changes in the temperature and other conditions in the environmental atmosphere on the accuracy of the measurement, preferably use is made of a constant current DC power supply circuit as the power source 22 in FIG. 1. More preferably the DC power source 22 includes a temperature compensation circuit.

Figure 2:
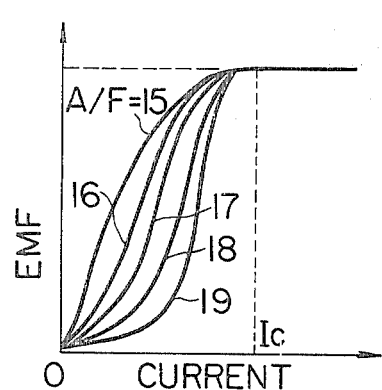
FIG. 2 is an explanatory graph showing variations of an electromotive force generated by the oxygen sensor of FIG. 1 when the sensor is disposed in the exhaust gas of an internal combustion engine operated with a lean mixture and supplied with a variable DC current.

When the oxygen sensing element 10 is disposed in an exhaust gas discharged from a gasoline engine operated with a lean air-fuel mixture, maintaining the exhaust gas temperature at the location of the sensing element 10 constantly at 550° C., with the reference electrode layer 16 connected to the negative terminal of the DC power source 22 (naturally the measurement electrode layer 18 to the positive terminal), the magnitude of EMF generated by the oxygen sensing element 10 varies with changes in the air/fuel ratio of the lean mixture fed to the engine and the intensity of the current supplied to the element 10 in the manner as shown in FIG. 2. As can be seen in FIG. 2, the magnitude of the EMF depends not only on the air/fuel ratio but also on the intensity of the DC current, and the EMF becomes substantially constant irrespective of values for the air/fuel ratio when the current intensity exceeds a critical value $I_c$. In other words, the magnitude of the EMF varies depending on the air/fuel ratio when the current intensity is kept constantly at a value smaller than the critical value $I_c$, so that an actual air/fuel ratio of the lean mixture can be detected by the oxygen sensing element 10 disposed in the exhaust gas.

Figure 3:
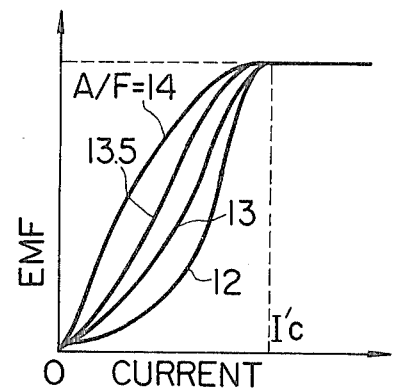
FIG. 3 is a graph similar to FIG. 2 but shows the variations when the engine is operated with a rich mixture and the direction of the current flow is reversed.

When the engine is operated with a rich mixture and the reference electrode layer 16 of the sensing element 10 is connected to the positive terminal of the DC power source 22, the dependence of the EMF on the air/fuel ratio and the current intensity becomes as shown in FIG. 3. Also in this case there exists a critical value $I_c'$ for the current intensity, and an actual air/fuel ratio can be detected by supplying a constant DC current smaller than the critical intensity $I_c'$ to the sensing element 10 in the exhaust gas.

We have recognized and experimentally confirmed the above explained facts. To summarize, we have confirmed that, when an oxygen sensor fundamentally constructed as described hereinbefore is used in an engine exhaust gas in the manner as shown in FIG. 1, there exists a critical current intensity ($I_c$ or $I_c'$) above which an EMF generated by the oxygen sensor does not vary unless the air/fuel ratio of a mixture fed to the engine changes across a stoichiometric ratio and that an actual air/fuel ratio different from the stoichiometric ratio can be detected with high accuracy by disposing the oxygen sensor in the exhaust gas and supplying a DC current smaller than the critical current intensity. Furthermore we have confirmed that, as will further be described later, the realization of the stoichiometric air/fuel ratio can be detected by using the same oxygen sensor generally in the same manner but supplying a current larger than the critical intensity to the sensor.

The principle of the operation of the oxygen sensing element 10 in an engine exhaust gas will be explained more in detail with reference to FIGS. 4–11.

Figure 4:
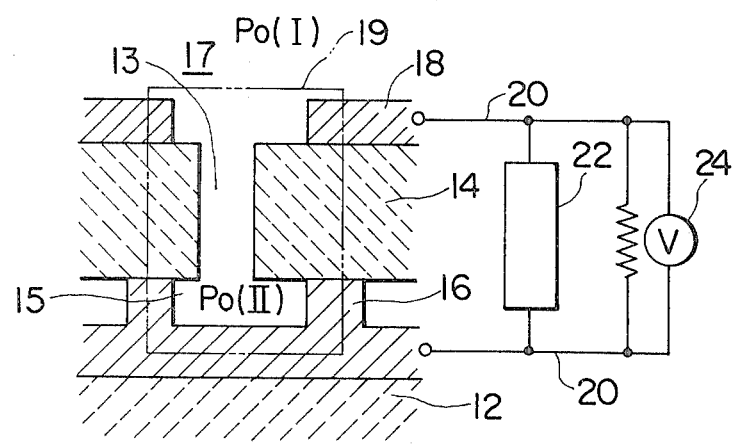
FIGS. 4, 6 and 7 are schematically enlarged illustrations of a microscopically small portion of the sensor of FIG. 1 for explanation of the principle of a method of the invention.

The solid electrolyte layer 14 of this sensing element 10 has an immense number of open micropores, and this element can be taken as an agglomeration of a large number of microscopic oxygen concentration cells (will be referred to simply as micro-cell) each having a through hole, i.e. a gas passage connecting the two electrode layers 16 and 18 across the solid electrolyte layer 14, provided by a fraction of the micropores. FIG. 4 illustrates one micro-cell 19 in a simplified form. By way of example, the solid electrolyte layer 14 is of $ZrO_2$—$Y_2O_3$ (9:1 mole ratio); both the reference and measurement electrode layers 16 and 18 are of platinum; and the shield layer or substrate 12 is of an alumina plate. Reference numeral 13 indicates a tiny through hole which provides communication between the reference electrode layer 16 and an external gas atmosphere (indicated by reference numeral 17), which is a combustion gas, subject to measurement through the measurement electrode layer 18 and the solid electrolyte layer 14. It may be considered that a terminal portion of this hole 13 provides a space 15 at the interface between the reference electrode layer 16 and the solid electrolyte layer 14.

Figure 5:
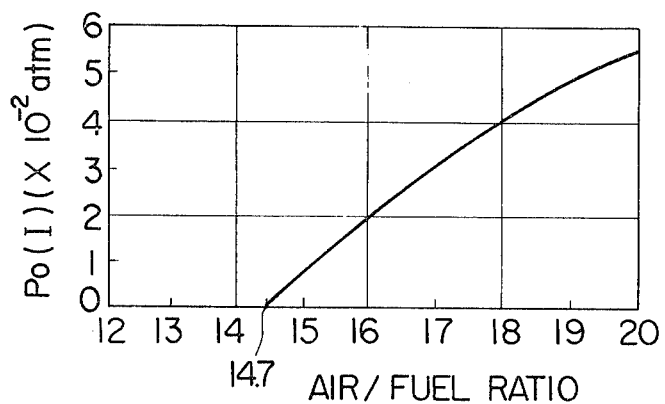
FIG. 5 is a graph showing the dependence of an oxygen partial pressure in an engine exhaust gas on the air/fuel ratio of a combustible mixture with which the engine is operated.

An electromotive force E generated by this micro-cell 19 is expressed by the Nernst Equation:

$$E = \frac{RT}{4F} \ln \frac{P_o(I)}{P_o(II)} \tag{1}$$

where $P_o(I)$ is an oxygen partial pressure in the sample gas 17 and $P_o(II)$ is an oxygen partial pressure in the space 15. Because of gas communication between the inner space 15 and the exterior gas atmosphere 17 through the hole 13, it is necessary to keep a DC current flowing between the two electrode layers 16 and 18 so as to cause electrolytic reactions (as will be described hereinafter) to continue on both sides of the solid electrolyte layer 14 thereby to maintain the reference oxygen partial pressure $P_o(II)$ constantly at a level different from the oxygen partial pressure $P_o(I)$ in the sample gas 17. The magnitude of oxygen partial pressure $P_o(I)$ in the combustion gas 17 depends on the air/fuel ratio of an air-fuel mixture from which the combustion gas 17 is produced. For an automobile gasoline engine, FIG. 5 shows the manner of dependence of the oxygen partial pressure $P_o(I)$ on the air/fuel ratio (by weight) of a lean mixture with which the engine is operated. Depending on the direction of the flow of this current, there occurs either the outflow of oxygen from the inner space 15 into the sample gas 17 or the inflow of oxygen into the space 15.

Figure 6:
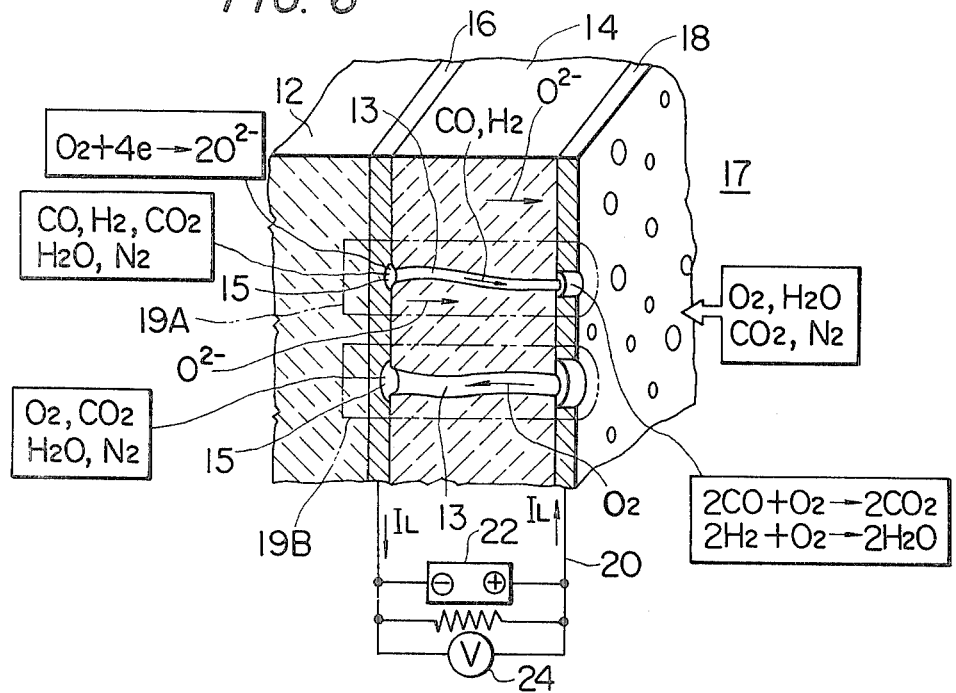

FIG. 6 illustrates a case where the combustion gas 17 is the product of the combustion of a lean air-fuel mixture and the reference electrode layer 16 of the probe 10, i.e. of a micro-cell 19A in this probe 10, is connected to the negative output terminal of the DC power source 22 so that a DC current $I_L$ flows through the solid electrolyte layer 14 from the measurement electrode layer 18 to the reference electrode layer 16. In this case oxygen tends to flow out of the micro-cell 19A through the following electrochemical phenomenon. Through the hole 13, $O_2$ contained in the combustion gas 17 arrives at the inner space 15 together with the other components such as CO, $CO_2$, $H_2O$ and $N_2$. However, there occurs ionization of oxygen molecules ($O_2 + 4e \rightarrow 2O^{2-}$) in this space 15, and the negatively charged oxygen ions migrate through the hole 13 towards the measurement electrode layer 18, wherein the current $I_L$ causes the oxygen ions to turn into oxygen molecules ($2O^{2-} \rightarrow O_2 + 4e$). Meanwhile, $CO_2$ and $H_2O$ arrived at the space 15 are electrolytically decomposed respectively to CO and $H_2$ ($CO_2 \rightarrow CO + \frac{1}{2}O_2$; $H_2O \rightarrow H_2 + \frac{1}{2}O_2$), followed by ionization of oxygen produced by the decomposition reactions. Thus, the space 15 is filled with a gas mixture containing little oxygen and large amounts of CO, $N_2$ and $H_2$, so that the reference oxygen partial pressure $P_o(II)$ in this case becomes of a very small magnitude, whereas the oxygen partial pressure $P_o(I)$ in the combustion gas 17 (which is produced by combustion of a lean air-fuel mixture and accordingly contains a considerable amount of oxygen) is of a relatively large magnitude. Therefore, the micro-cell 19A generates an electromotive force of a relatively large magnitude. If the combustion gas 17 is the product of the combustion of a rich air-fuel mixture while the probe 10 is connected to the DC power source 22 as shown in FIG. 7, the probe 10 can generate only a very small electromotive force since in such a case not only the reference oxygen partial pressure $P_o(II)$ but also the oxygen partial pressure $P_o(I)$ in the combustion gas 17 becomes very low.

Figure 7:
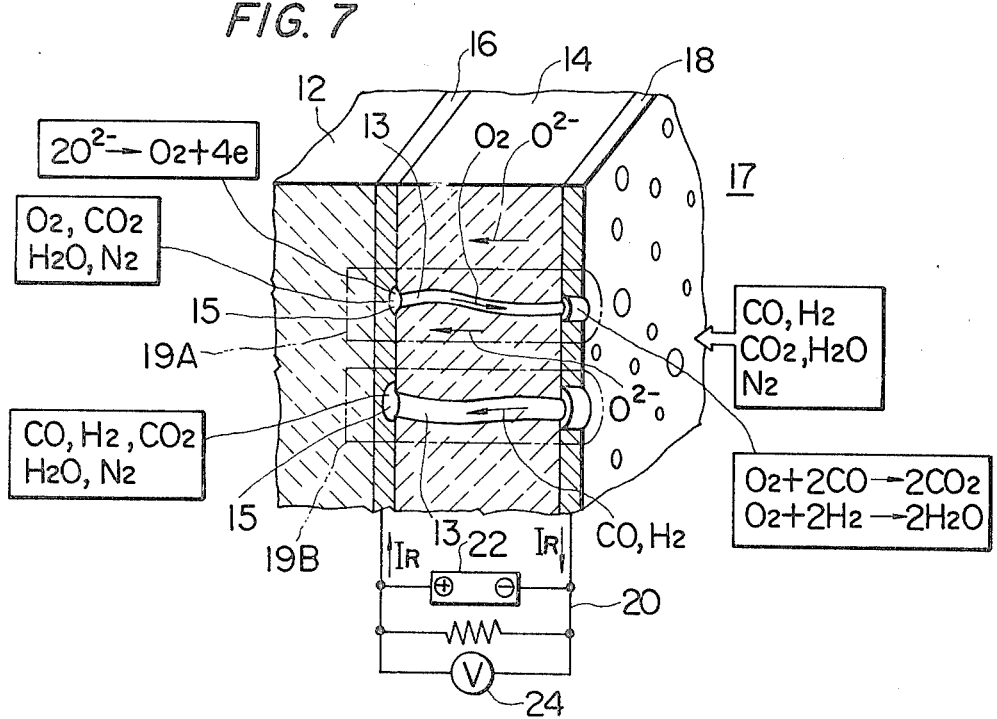

In FIG. 7, the reference electrode layer 16 of the same oxygen sensing probe 10 is connected to the positive output terminal of the DC power source 22 so that a current $I_R$ flows through the solid electrolyte layer 14 from the reference electrode layer 16 to the measurement electrode layer 18. The combustion gas 17 is assumed to be produced by the combustion of a rich air-fuel mixture. In this case oxygen molecules contained in the combustion gas are ionized in the measurement electrode layer 18, and the negatively charged oxygen ions migrate through the hole 13 towards the reference electrode layer 16, i.e. into the aforementioned space 15, wherein the oxygen ions are deprived of their electrons to turn into oxygen molecules. As a consequence, the reference oxygen partial pressure $P_o(II)$ in this case is of a considerably large magnitude, whereas the combustion gas 17 is very low in its oxygen partial pressure $P_o(I)$. A micro-cell 19A, therefore, generates a relatively large electromotive force. If the combustion gas 17 in FIG. 7 is the product of the combustion of a lean air-fuel mixture, the micro-cell 19A can generate only a very small electromotive force.

In addition to the above explained electrolytic reactions occurring on both sides of the solid electrolyte layer 14, certain oxidation reactions take place in the hole 13 through which occurs diffusion exchange of gaseous substances between the exterior gas atmosphere 17 and the interior space 15. In the case of FIG. 6, some portions of CO and $H_2$ produced in the reference electrode layer 16 are oxidized (respectively to $CO_2$ and $H_2O$) during their outflow through the hole 13 by $O_2$ entering the hole 13 from the exterior gas atmosphere 17. In the case of FIG. 7, CO and $H_2$ flowing in the hole 13 towards the reference electrode layer 16 are oxidized by a portion of $O_2$ formed in the space 15. The degree of significance of these oxidation reactions in the hole 13 depends on the quantities of the gaseous substances passing through the hole 13 and hence on the effective cross-sectional area of the hole 13. It will be understood that a micro-cell 19B in which the hole 13 has an unduly large cross-sectional area can hardly generate an electromotive force since the reference oxygen partial pressure $P_o(II)$ in this micro-cell 19B becomes almost equal to the oxygen partial pressure $P_o(I)$ in the exterior gas atmosphere 17.

As will be understood from the foregoing description with reference to FIGS. 4–7, the EMF generating ability of each micro-cell 19 in this oxygen sensing probe 10 is influenced not only by the oxygen concentration in the exterior gas atmosphere 17 and the direction and intensity of the current ($I_L$ or $I_R$) flowing through the cell 19 but also by the amounts of CO, $H_2$, $CO_2$ and $H_2O$ contained in the gas 17 and the effectiveness of the hole 13 as a gas diffusion passage. Since the numerous holes 13 in the probe 10 are usually different from one another in their effective cross-sectional area and/or length, it is quite likely that, either in the case of FIG. 6 or in the case of FIG. 7, some of the entire total micro-cells 19 in the probe 10 generate substantially no electromotive force (as represented by the micro-cell 19B in FIGS. 6 and 7) while the remaining micro-cells 19 (represented by the micro-cells 19A in FIGS. 6 and 7) each generate a considerably large electromotive force. In the probe 10 in operation, a micro-cell (19A) which duly generates an electromotive force will be called "live micro-cell", and a micro-cell (19B) which generates substantially no electromotive force will be called "dead micro-cell".

The proportion of the live micro-cells 19A to the dead micro-cells 19B in the probe 10 is determined mainly by the oxygen concentration in the sample gas 17, the direction and intensity of the current $I_L$ or $I_R$ and the manner and scale of gas diffusion through the hole 13 in each micro-cell 19. When the probe 10 is disposed in a combustion gas of a definite composition and is supplied with a definite DC current, the ease of the gas diffusion depends on the effective cross-sectional area of the hole 13 in each micro-cell 19, the effective length of each hole 13, the temperatures of gaseous substances passing through each hole 13 and the diffusion constant of each of the gaseous substances passing through the hole 13 as will hereinafter be described more in detail.

If the entire micro-cells 19 in the probe 10 were identical in the cross-sectional area and length of their holes 13, there will occur either a case where all the micro-cells 19 in the probe 10 supplied with an appropriate DC current assume the live state or a contrary case where all the micro-cells 19 assume the dead state depending on the magnitude of the oxygen partial pressure $P_o(I)$ in the gas 17, meaning that the probe 10 can exhibit an on-off function and can indicate a change in the air/fuel ratio across a definite value. In reality, however, the micro-cells 19 in the probe 10 are rarely identical in the dimensions of the holes 13. When (as is usual) the holes 13 in the probe 10 are different in size from one another and the hole size exhibits a continuous dispersion, both the live micro-cells 19A and dead micro-cells 19B will exist in the probe 10 in operation, and the proportion of the live micro-cells 19A to the dead micro-cells 19B will vary continuously according to the external factors such as the intensity of the current $I_L$ or $I_R$ and the oxygen partial pressure $P_o(I)$ in the sample gas 17. Then, the probe 10 will produce a continuously variable output in response to a continuous change in the oxygen partial pressure $P_o(I)$ or air/fuel ratio of an air-fuel mixture from which the combustion gas 17 is produced. This presumption was confirmed by us to be realizable and has become a keypoint of the present invention.

Even though the holes 13 in the probe 10 are different from one another in size, the intensity of the current supplied to the probe 10 significantly influences the proportion of the live micro-cells 19A to the dead micro-cells 19B. The proportion of the live micro-cells 19A increases as the current intensity is increased, and when the current intensity exceeds a certain critical value all the micro-cells 19 in the probe 10 function as the live micro-cells 19A. (The above quoted prior Application teaches the use of the probe 10 in such a state.)

When the intensity of the current $I_L$ in FIG. 6 or $I_R$ in FIG. 7 is appropriate to keep a portion of the micro-cells 19 in the probe 10 in the live state, whether each micro-cell 19 becomes live or dead will depend on the relation between the quantity (or flow rate) $J_i$ of $O_2$ flowing in the hole 13 of this micro-cell 19 either towards the reference electrode layer 16 or towards the measurement electrode layer 18 and the quantity (or flow rate) $J_g$ of an oxidizable reactant gas (such as a mixture of CO and $H_2$) diffusing into or from this micro-cell 19 through its hole 13. When the difference $\Delta J = J_i - J_g$ is positive ($\Delta J > 0$) the micro-cell 19 becomes live and generates an electromotive force, but if the difference $\Delta J$ is negative ($\Delta J < 0$) the micro-cell 19 becomes dead and generates substantially no electromotive force.

The quantity $J_i$ of oxygen represents either the rate of electrolytical formation of $O_2$ or the rate of ionization of $O_2$ in each micro-cell 19 and hence depends on the intensity of the current $I_L$ or $I_R$. The quantity $J_g$ of the reactant gas is expressed by the following equation according to Fick's first law:

$$J_g = D(S/L)[P_o(I) - P_o(II)] \quad (2)$$

where D is the diffusion constant of the reactant gas, S is an effective cross-sectional area of the hole 13, and L is an effective length of the hole 13.

Assuming that the mean free path of the reactant gas molecules is sufficiently large compared with the diameter Q of the hole 13 and that the reactant gas flows into the hole 13 at a sufficiently great rate by Knudsen diffusion, the diffusion constant D is expressed by $$D = 9.7 \times 10^3 Q\sqrt{T/M} \text{(cm}^2\text{/sec)} \quad (3)$$

where M represents the molecular weight of the reactant gas. Then $J_g$ is expressed by $$J_g = 9.7 \times 10^3 \sqrt{(T/M)} (\pi Q^3/L)[P_o(I) - P_o(II)] \quad (4)$$

Equation (4) shows that $J_g$ becomes larger as the hole diameter Q increases, as the pore length L decreases, and as the temperature T increases and hence the probability of the micro-cell 19 assuming the dead state becomes larger.

A further analysis will be made with respect to a variation in the hole diameter Q assuming that the hole length L and the gas temperature T are constant.

The total number of the micro-cells 19 in the probe 10 will be represented by N, the number of the live micro-cells 19A by $n_L$, and the number of the dead micro-cells 19B by $n_D$ (accordingly $N = n_L + n_D$). Then an electromotive force $E_t$ generated by the probe 10 as a whole can be expressed approximately by the following equation:

$$E_t = (n_L/N)E_1 \quad (5)$$

where $E_1$ represents an electromotive force generated by a single live micro-cell 19A. (Usually $E_1$ is close to 1 volt.)

In the case of FIG. 6 (the reference electrode layer 16 is connected to the negative terminal of the DC power source 22, and the combustion gas 17 is the product of a lean air-fuel mixture, having an excess air factor λ (the ratio of the air/fuel ratio of this mixture to the stoichiometric air/fuel ratio) greater than 1.0, the quantity $J_g$ of a reactant gas flowing through the hole 13 of each micro-cell 19 increases as the air/fuel ratio of the air-fuel mixture increases because of an increase in the oxygen concentration in the combustion gas 17, so that the number $n_D$ of the dead micro-cells 19B increases (naturally the number $n_L$ of the live micro-cells 19A decreases) as the air/fuel ratio increases. The above defined electromotive force $E_1$ may be assumed to remain constant while the proportion of $n_L$ to $n_D$ decreases with increase in the air/fuel ratio.

Figure 8:
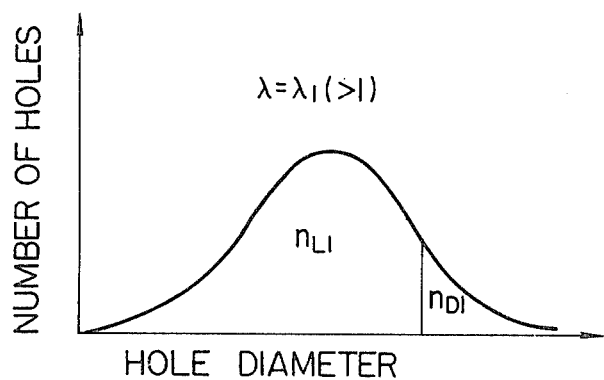
FIGS. 8 and 9 show graphically a variation in the ratio of effectual micropores to ineffectual micropores in the sensor of FIG. 1 depending on the mode of using this sensor.
Figure 9:
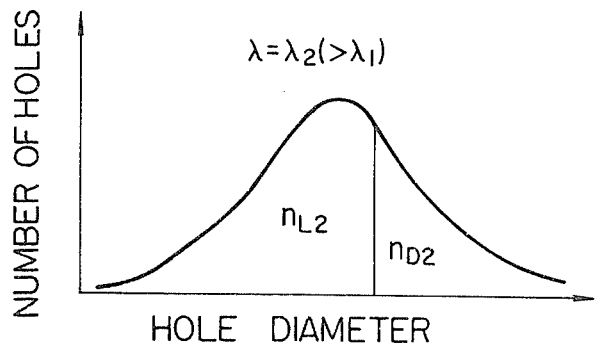

FIG. 8 shows the distribution of the hole diameter Q in the probe 10 in FIG. 6 and the proportion of $n_L$ to $n_D$ in this probe 10 when the excess air factor λ of the lean air-fuel mixture takes a value $\lambda_1$ somewhat greater than 1.0. Under this condition, the number $n_L$ of the live micro-cells 19A and the number $n_D$ of the dead micro-cells 19B in this probe 10 become $n_{L1}$ and $n_{D1}$, respectively (of course $n_{L1} + n_{D1} = N$). Referring to FIG. 9, when the air/fuel ratio increases so that λ becomes $\lambda_2$ ($> \lambda_1$), the number of the dead micro-cells 19B increases from $n_{D1}$ in FIG. 8 to $n_{D2}$ with decrease of the number of the live micro-cells 19A from $n_{L1}$ to $n_{L2}$ ($n_{L2} + n_{D2} = N$).

Figure 10:
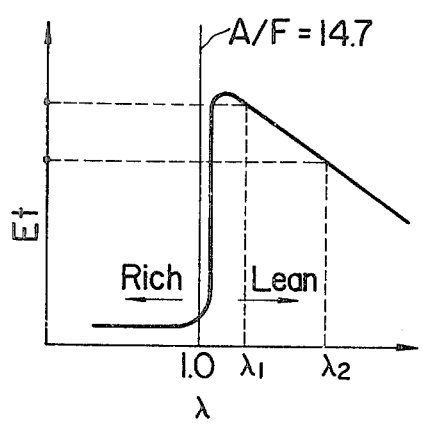
FIGS. 10 and 11 are graphs showing a variation in the output characteristic of the sensor of FIG. 1 depending on the mode of using this sensor.

Due to such a change in the proportion of $n_L$ to $n_D$, the magnitude of the electromotive force $E_t$ generated by the probe 10 in FIG. 6 varies as shown in FIG. 10 as the air/fuel ratio, i.e. excess air factor λ, changes. Where the excess air factor λ is greater than 1.0, meaning that the combustion gas 17 is produced from a lean air-fuel mixture, the probe 10 in FIG. 6 (with the supply of the current $I_L$ of an appropriate intensity) exhibits a continuous change in the magnitude of electromotive force $E_t$ in response to a continuous change in the air/fuel ratio or excess air factor λ. Accordingly, it is possible to detect not only the occurrence of a change in the air/fuel ratio of the lean air-fuel mixture but also an actual numerical value for the air/fuel ratio at any moment.

In the case of FIG. 7 (the reference electrode layer 16 of the probe 10 is connected to the positive terminal of the DC power source 22, and the combustion gas 17 is produced by combustion of a rich air-fuel mixture, λ < 1.0), it will be understood that the probe 10 (supplied with the current $I_R$ of an appropriate intensity) exhibits a continuous change in the magnitude of electromotive force $E_t$ in response to a continuous change in the air/fuel ratio of the rich air-fuel mixture.

Figure 11:
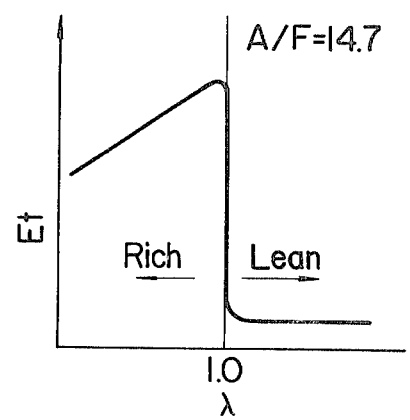

As described hereinbefore with reference to FIGS. 2 and 3, when the probe 10 either in FIG. 6 or in FIG. 7 is supplied with a current greater than the critical current intensity ($I_c$ or $I_c'$) the probe 10 generates a substantially constant electromotive force unless λ changes across 1.0 because the difference ΔJ between $J_i$ and $J_g$ remains always positive (ΔJ > 0) when such a great current flows through each micro-cell 19. In this state, the probe 10 serves as an on-off type sensor which indicates the occurrence of a change in the air/fuel ratio across a stoichiometric ratio, that is, a change of a lean air-fuel mixture to a rich mixture, or a reverse change. An output characteristic as shown in FIG. 10 or 11 is realized while the current $I_L$ in FIG. 6 is smaller than $I_c$ in FIG. 2, or the current $I_R$ in FIG. 7 is smaller than $I_c'$ in FIG. 3.

The invention will be further illustrated by the following examples.

EXAMPLE 1

FIGS. 12(A) to 12(E) show a process of fabricating an oxygen sensing probe 50 which is fundamentally of the construction shown in FIG. 1.

Referring to FIG. 12(A), a shield layer or substrate 32 of this probe 50 was an about 3.4 × 5 mm wide and 1.6 mm thick alumina plate, and 0.2 mm platinum wires 40 were attached to this substrate 32 so as to serve as a pair of leads of this probe 50. As shown in FIG. 12(B), a paste containing a platinum powder dispersed in an organic binder was printed on one side of the alumina substrate 32 and, after drying in air at 100° C. for 20 min, was subjected to baking in air at a temperature of 1300° C. for a period of 1 hr thereby to form a porous reference electrode layer 36 of platinum having a thickness of 1~2 μm. Then, a solid electrolyte paste prepared by dispersing 1 part by weight of finely powdered $ZrO_2$—$Y_2O_3$ system (92:8 by weight, 0.5 μm in mean particle size) in 1 part by weight of an organic binder (lacquer) was printed on the substrate 32 so as to cover the platinum electrode layer 36 as shown in FIG. 12(C). After drying in air at 100° C. for 30 min, the paste-applied substrate 32 was baked in air at 1380° C. for 3 hr to sinter the $ZrO_2$—$Y_2O_3$ powder in the paste into a porous solid electrolyte layer 34, which was 20 μm in thickness. Then a porous measurement electrode layer 38 of platinum was formed on a major area of the solid electrolyte layer 34 as shown in FIG. 12(D) by the method used to form the reference electrode layer 36. The thus treated element was entirely coated with a porous protective layer 42 shown in FIG. 12(E) by plasma spraying of a calcium zirconate powder.

Referring to FIG. 13, an oxygen sensor was produced by assembling the oxygen sensing probe 50 of FIG. 12(E) with a tubular holder 52, a hood 56 formed with apertures 56a and a tubular and flanged attachment 58. Reference numeral 54 indicates an alumina rod having axial bores through which extend the leads 40. The interior of the attachment 58 was occupied by a metal tube 60 filled with a heat-resistant sealant 62.

The oxygen sensor of FIG. 13 was attached to an exhaust pipe of an automotive gasoline engine so that the probe 50 was exposed to the exhaust gas through the apertures 56a of the hood 56, and the reference electrode layer 36 of the probe 50 was connected to the negative terminal of a DC power source and the measurement electrode layer 38 to the positive terminal. A potentiometer used to measure an electromotive force generated by the sensor had an internal impedance of 1 megohm. To examine the performance of the sensor, the air/fuel ratio of an air-gasoline mixture for operation of the engine was varied within the range from 13 to 19.5, and the intensity of the current flowing through the probe 50 was varied within the range from 1 μA to 15 μA. The experiment was carried out such that the exhaust gas temperature at the location of the oxygen sensor was constantly 550° C. The result of this experiment is presented in FIG. 14.

Figure 14:
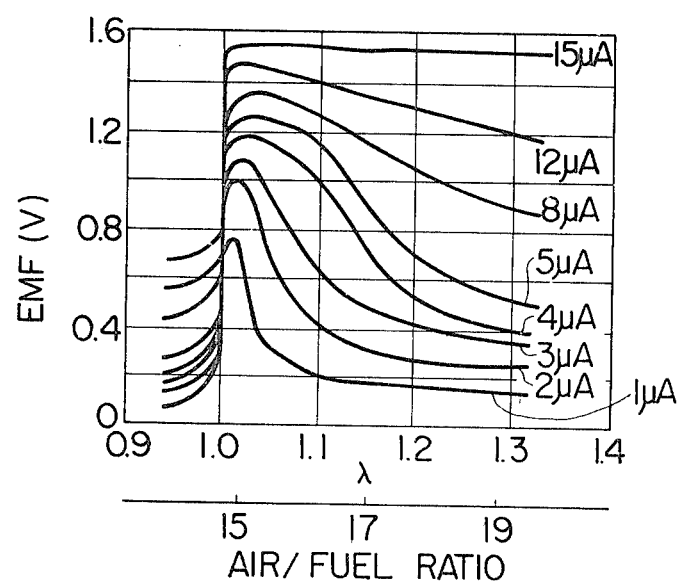
FIGS. 14–17 are graphs showing variations in the output of the oxygen sensor of FIG. 13 with variations in the content of oxygen in an engine exhaust gas subjected to measurement and/or in a DC current supplied to the sensor.

As can be seen in FIG. 14, the critical intensity $I_c$ (above which the EMF became substantially constant insofar as a lean air-fuel mixture was supplied to the engine) for the oxygen sensing probe 50 in this experiment was 15 μA. When the probe 50 was operated with the supply of a current smaller than 15 μA, the output of the probe 50 exhibited a good response in its output to changes in the air/fuel ratio of a lean air-fuel mixture, and the response was very clear and faithful when the intensity of the current was in the range from about 20% to about 80% of the critical current intensity, 15 μA.

EXAMPLE 2

A comparison between the oxygen sensor produced in Example 1 and a conventional oxygen sensor which comprised a zirconia tube and utilized air as the source of a reference oxygen partial pressure. These two sensors were both attached to an exhaust pipe of an automotive gasoline engine, and the air/fuel ratio of an air-fuel mixture fed to the engine was varied within the range from 13.7 to 17.3. The exhaust gas temperature at the location of the sensors was maintained constantly at about 600° C. A constant current of 3 μA was supplied to the sensor of FIG. 13 by connecting the reference electrode layer 36 to the negative terminal of a DC power source. Of course the conventional sensor of the zirconia tube type was used without supplying any external current.

Figure 15:
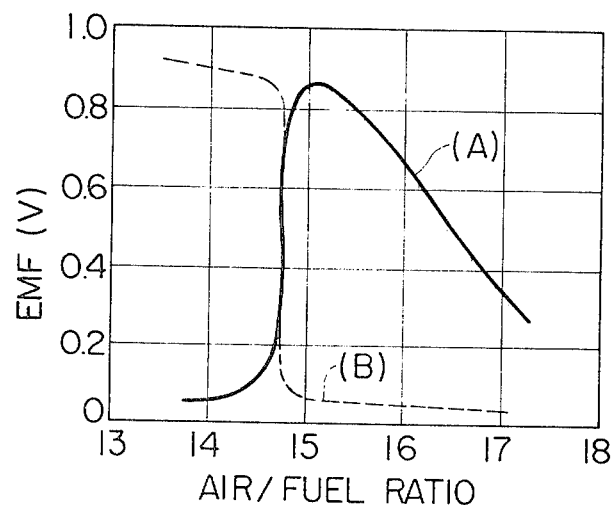

The result of this comparative experiment is shown in FIG. 15, wherein the curve (A) represents the sensor of FIG. 13 and the curve (B) the conventional sensor of the zirconia tube type. As can be seen clearly in FIG. 15, the output of the sensor of FIG. 13 exhibited a great and continuous change as the air/fuel ratio was varied in a lean range, whereas the conventional sensor exhibited little change in its output except when the air/fuel ratio was varied across the stoichiometric ratio, 14.7.

EXAMPLE 3

Figure 16:
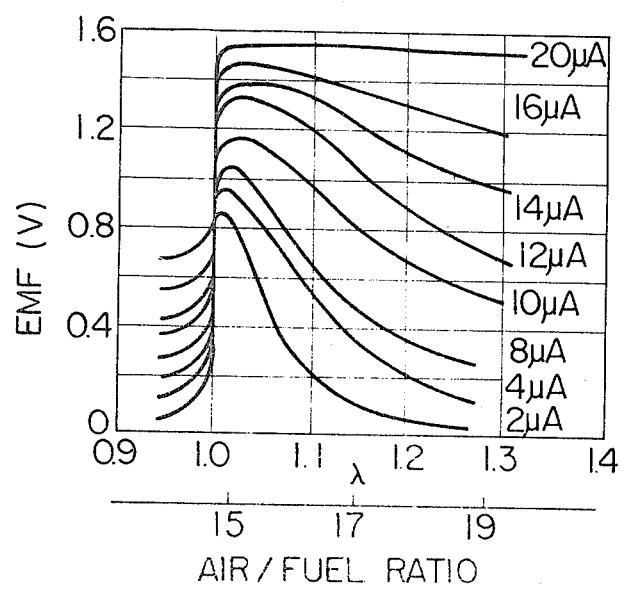

To examine the temperature dependence of the output characteristic of the oxygen sensing probe 50 produced in Example 1, the experiment described in Example 1 was repeated except that the exhaust gas temperature at the location of the exygen sensor was raised to 700° C. The result is shown in FIG. 16. As shown, in this case the critical current intensity $I_c$ was about 20 μA, and the manner of the response of the sensor to changes in the air/fuel ratio in a lean range was particularly good when a current ranging from about 4 to about 16 μA was supplied to the probe 50.

EXAMPLE 4

This example, too, was generally similar to Example 1, except that the thickness of the solid electrolyte layer 34 was 10 μm and that a constant exhaust gas temperature of 600° C. was maintained at the location of the oxygen sensor.

Figure 17:
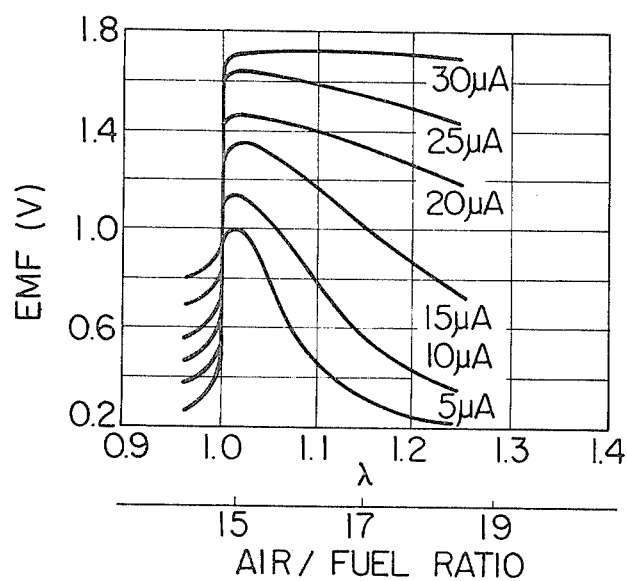

FIG. 17 shows the output characteristic of the oxygen sensor produced and tested in Example 4. In this case, the critical current intensity $I_c$ was judged to be about 30 μA. With the supply of a smaller current, the sensor gave accurate indications of air/fuel ratios higher than the stoichiometric ratio.

EXAMPLE 5

Figure 18:
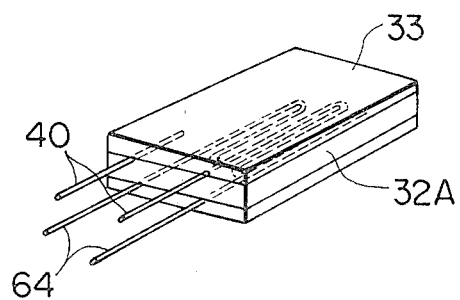
FIG. 18 is a perspective view of an oxygen sensing element which is a modification of the sensing element shown in FIG. 12(E)

Referring to FIG. 18, a substrate 32A for an oxygen sensing probe fundamentally of the same construction as the probe 50 of FIG. 12(E) was prepared from three sheets of thin alumina green plates. First, 0.25 mm heater wire 64 of platinum was sandwiched between two alumina plates. Then a pair of lead wires 40 (0.25 mm platinum wires) were placed on an outer surface of the piled alumina plates, and the third alumina plate was piled on the same surface so as to cover the lead wires 40. In this state the entire assembly was fired in air for 2 hr at 1500° C. On one side 33 of the thus obtained substrate 32A, a reference electrode layer of platinum, a solid electrolyte layer of $ZrO_2$—$Y_2O_3$ and a measurement electrode layer of platinum were formed in turn exactly by the process of Example 1 illustrated in FIGS. 12(A) to 12(D). Accordingly, the oxygen sensing probe produced in Example 5 could be regarded as the addition of the heater 64 to the probe 50 of FIG. 12(E). The resistance of this heater 64 was 1 ohm at room temperature.

The performance of this oxygen sensing element in the exhaust gas of an automotive gasoline engine was examined by a test fundamentally similar to the test in Example 1. The probe was operated with the supply of a constant current of 3 μA by connecting the reference electrode layer to the negative terminal of the DC power source, and a controlled current is supplied to the heater 64 to maintain the surface temperature of the probe constantly at 600° C. with the accuracy of ±5° C. based on actual temperatures estimated from the resistance of the heater wire 64. The air/fuel ratio for operating the engine was varied stepwise within the range from about 15 to about 18.

Figure 19:
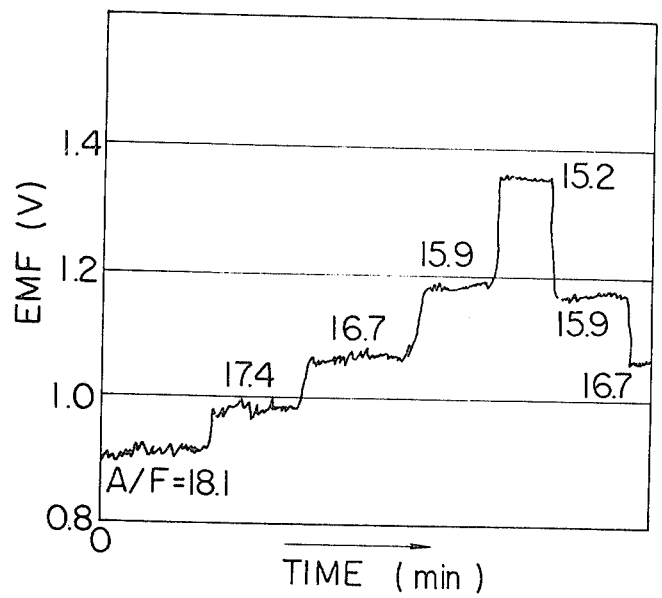
FIGS. 19 and 20 are graphs showing variations in the output characteristic of the oxygen sensing element of FIG. 18 with variations in the content of oxygen in an exhaust gas subjected to measurement and/or in a DC current supplied to the sensing element.

The result of this test, as shown in FIG. 19, demonstrates that the tested probe is excellent in its response to changes in the air/fuel ratio of a lean air-fuel mixture and is quite suitable for practical applications to lean-burn-engines.

EXAMPLE 6

The oxygen sensing probe produced in Example 5 was tested generally according to the test method in Example 1 except that the reference electrode layer of the probe was connected to the positive terminal of the DC power source, that the air/fuel ratio was varied within the range from 12 to 15.7 and that the temperature of the probe was maintained at about 600° C.

Figure 20:
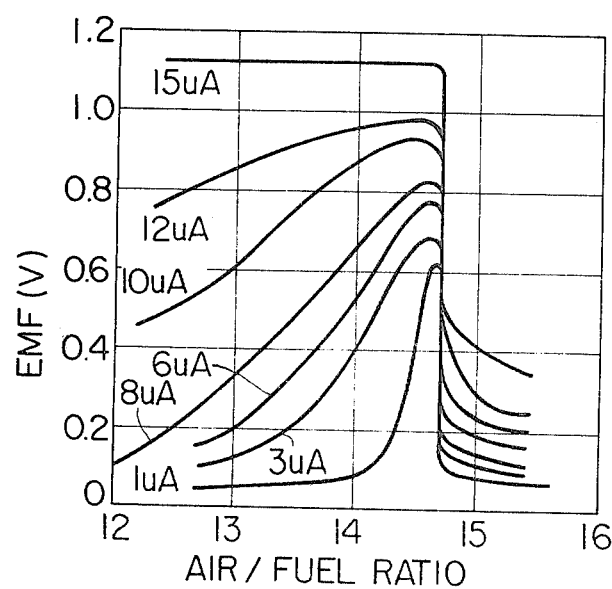

FIG. 20 shows the result of this test. As can be seen in FIG. 20, the output of the probe varied in good response to changes in the air/fuel ratio of a rich air-fuel mixture fed to the engine when a current smaller than about 15 $\mu$A was supplied to the probe, and the probe exhibited a particularly favorable output characteristic when operated with the supply of a current in the range from about 3 $\mu$A to about 12 $\mu$A, i.e. a current ranging from about 20 to about 80% of the critical current intensity $I_c'$ (15 $\mu$A).

What is claimed is:

1. A method of detecting an air/fuel ratio of an air-fuel mixture subjected to combustion in an apparatus having a combustion chamber and an exhaust conduit through which passes a combustion gas produced by combustion of the air-fuel mixture, the method comprising the steps of:

disposing an oxygen sensing probe in said exhaust conduit so as to be contacted with said combustion gas, said probe comprising a gas permeably porous layer of an oxygen ion conductive solid electrolyte, a gas permeably porous and electronically conductive reference electrode layer formed on and in intimate contact with one side of the solid electrolyte layer, a gas permeably porous and electronically conductive measurement electrode layer formed on and in intimate contact with the other side of said solid electrolyte layer and a shield layer which is made of an electrochemically inactive material and covers said reference electrode layer such that said reference electrode layer communicates with an environmental gas atmosphere only through pores in said measurement electrode layer and said solid electrolyte layer;

applying continuously a DC voltage to said reference and measurement electrode layers so as to keep a DC current of a predetermined intensity flowing through said solid electrolyte layer between said reference electrode layer and said measurement electrode layer thereby to maintain a reference oxygen partial pressure at the interface between said reference electrode layer and said solid electrolyte layer; and measuring an electromotive force generated across said reference electrode layer and said measurement electrode layer thereby to detect said air/fuel ratio based on a predetermined relationship between said air/fuel ratio and the magnitude of said electromotive force;

said predetermined intensity of said current being smaller than a critical current intensity above which the magnitude of said electromotive force becomes substantially constant while said air/fuel ratio changes on one side of but does not cross the stoichiometric air/fuel ratio of said air-fuel mixture.

2. A method according to claim 1, wherein said voltage is applied to said probe by connecting said reference electrode layer and said measurement electrode layer respectively to the negative terminal and to the positive terminal of a DC power source, said air/fuel ratio of said air-fuel mixture being expected to remain above said stoichiometric air/fuel ratio.

3. A method according to claim 1, wherein said voltage is applied to said probe by connecting said reference electrode layer and said measurement electrode layer respectively to the positive terminal and to the negative terminal of a DC power source, said air/fuel ratio of said air-fuel mixture being expected to remain below said stoichiometric air/fuel ratio.

4. A method according to claims 2 or 3, wherein said predetermined intensity of said current is in the range from about 20% to about 80% of said critical current intensity.

5. A method according to claim 1, further comprising the step of heating said probe disposed in said exhaust conduit by means of an electric heater attached to said probe so as to maintain said probe at a nearly constant temperature.

6. A method according to claim 1, wherein said reference electrode layer and said measurement electrode layer are each made of a metal which exhibits a catalytic action on oxidation reactions.

7. A method according to claim 1, wherein said shield layer takes the form of a plate and serves as a structurally basic member of said probe, said solid electrolyte layer, said reference electrode layer and said measurement electrode layer being each in the form of a relatively thin film.

8. A method of detecting an oxygen concentration in a combustion gas which is produced by combustion of an air-fuel mixture in an apparatus having a combustion chamber and is passing through an exhaust passage extending from the combustion chamber, the method comprising the steps of:

disposing an oxygen sensing probe in said exhaust conduit so as to be contacted with said combustion gas, said probe comprising a gas permeably porous layer of an oxygen ion conductive solid electrolyte, a gas permeably porous reference electrode layer formed on and in intimate contact with one side of the solid electrolyte layer, a gas permeably porous measurement electrode layer formed on and in intimate contact with the other side of said solid electrolyte layer and a shield layer which is made of an electrochemically inactive material and covers said reference electrode layer such that said reference electrode layer communicates with an environmental gas atmosphere only through pores in said measurement electrode layer and said solid electrolyte layer;

applying continuously a DC voltage to said reference and measurement electrode layers so as to keep a DC current of a predetermined intensity flowing through said solid electrolyte layer between said reference electrode layer and said measurement electrode layer thereby to maintain a reference oxygen partial pressure at the interface between said reference electrode layer and said solid electrolyte layer;

measuring an electromotive force generated across said reference electrode layer and said measurement electrode layer thereby to detect said oxygen concentration based on a preexamined relationship between said oxygen concentration and the magnitude of said electromotive force;

said predetermined intensity of said current being smaller than a critical current intensity above which the magnitude of said electromotive force becomes substantially constant while the air/fuel ratio of said air-fuel mixture changes on one side of but does not cross the stoichiometric air/fuel ratio of said air-fuel mixture.

* * * * *